United States Patent [19]

Lovick

[11] 4,120,301

[45] Oct. 17, 1978

[54] APPARATUS FOR SURGICAL PROCEDURES INVOLVING ANIMALS

[76] Inventor: James Shepperd Lovick, Henderson, Tex. 75652

[21] Appl. No.: 739,501

[22] Filed: Nov. 8, 1976

[51] Int. Cl.[2] .............................................. A61B 17/00

[52] U.S. Cl. ................................. 128/303 R; 128/306

[58] Field of Search ................. 128/20, 132 R, 303 R, 128/306

[56] References Cited

U.S. PATENT DOCUMENTS

| | | | |
|---|---|---|---|
| 1,550,403 | 8/1925 | Turkus | 128/303 R |
| 1,615,125 | 1/1927 | Lespinasse | 128/306 X |
| 2,050,449 | 8/1936 | Muter et al. | 128/306 |
| 2,822,802 | 2/1958 | Corriero | 128/20 |

*Primary Examiner*—Robert W. Michell
*Assistant Examiner*—Michael H. Thaler

[57] ABSTRACT

An apparatus for use in the castration of an animal comprising a relatively thin shield having an aperture disposed within the shield to allow the scrotum of the animal to extend through the shield. Adjustable jaws, or shoulders, engage and restrain the scrotum in a predetermined position adjacent the upper surface of the shield. A spermatic cord retaining means engages and restrains the spermatic cord of the animal in a predetermined position when a testicle is withdrawn from the scrotum.

7 Claims, 5 Drawing Figures

APPARATUS FOR SURGICAL PROCEDURES INVOLVING ANIMALS

BACKGROUND OF THE INVENTION

This invention relates to an apparatus for use in certain surgical procedures involving animals. In another aspect, this invention relates to an apparatus that is used in the castration of animals to allow the castration procedure to be carried out under sanitary conditions and without an operating assistant. In still another aspect, this invention relates to an apparatus for use in the castration of feline animals whereby the procedure is carried out without an operating assistant.

Surgical procedures to castrate various animals are widely used. Recently, there has been an awareness of overpopulation of many animals, such as domestic animals, and, in order to control such reproduction, castration of male animals has been carried out on a large scale. Additionally, it is well known that castration of some male animals improves the health and growing characteristics of such animals, as well as their temperament.

Castration of male animals is normally carried out by either restraining the animal in a prone position or by anesthetizing the animal and, thereafter, surgically removing the testicles from the scrotum of the animal. Unfortunately, operations involving the physical restraint of the animal must be carried out with the aid of several people or with the aid of elaborate physical restraining means to properly restrain the animal. Therefore, by anesthetizing the animal to be castrated, it is possible to carry out the surgical removal of the testicles by utilizing fewer people. However, even when the animal is anesthetized, castration procedures normally involve at least two people. In carrying out the castration of animals using conventional techniques and equipment, the procedure is normally one wherein an incision is made in the scrotum of the animal followed by the pulling of the testicle from the scrotum to expose the spermatic cord that is attached to the animal. Generally, the spermatic cord is tied closed with suitable suturing material or otherwise closed with clamps and the like, and then the spermatic cord is severed intermediate the tie or clamp and the testicle. Normally, the spermatic cord will be pulled back into the incision in the scrotum following such suturing or clamping and cutting.

Unfortunately, by utilizing the above-mentioned conventional techniques and equipment, the castration of animals still involves at least two people wherein it is necessary for one person to withdraw the testicle from the scrotum and hold it in a predetermined position while the other operating party either ties the spermatic cord shut or clamps it shut and thereafter severs the spermatic cord. An additional problem is evident in that the castration of animals is complicated by the presence of fur, hair, dirt, and other foreign bodies in the area of the operation. All of the foregoing problems connected with castration of male animals are especially applicable to the castration of male feline animals, wherein it is extremely difficult, if not impossible, to carry out the castration of the male feline animals without two parties participating in the operation.

It is, therefore, recognized that there is a need for improved apparatus and equipment for use in castration procedures on animals to allow the procedures to be carried out by only one person and to allow the procedures to be carried out under more sanitary conditions.

SUMMARY OF THE INVENTION

Accordingly, it is an object of this invention to provide an improved apparatus for carrying out certain surgical procedures involving animals. It is another object of this invention to provide an apparatus for use in castration of animals to eliminate the necessity of two people to participate in the operation.

It is yet another object of this invention to provide an apparatus for the castration of animals wherein the procedure can be carried out under more sanitary conditions. It is yet another object of this invention to provide an appparatus for use in the castration of feline animals wherein the procedure can be carried out by one person under sanitary conditions.

Other aspects, objects and advantages of this invention will be apparent to those skilled in the art from the following disclosure and appended claims.

The instant invention is an apparatus for use in certain surgical procedures involving animals such as in the castration of male animals. The apparatus of the invention generally comprises a shield means that has an upper surface and a lower surface with an aperture extending through the shield means of sufficient size and shape to receive the scrotum of the animal whereby the scrotum extends upwardly through and is adjacent the upper side of the shield means when the apparatus is in place. The apparatus also includes a scrotum retaining means adapted to engage and restrain the scrotum adjacent the upper surface of the shield means as the scrotum is pulled through the aperture. A spermatic cord restraining means is operably connected to the shield means and is adapted to engage and restrain the spermatic cord of the animal in a predetermined position above the upper surface of the shield means when a testicle is withdrawn from the scrotum.

DESCRIPTION OF PREFERRED EMBODIMENTS

Figure 1:
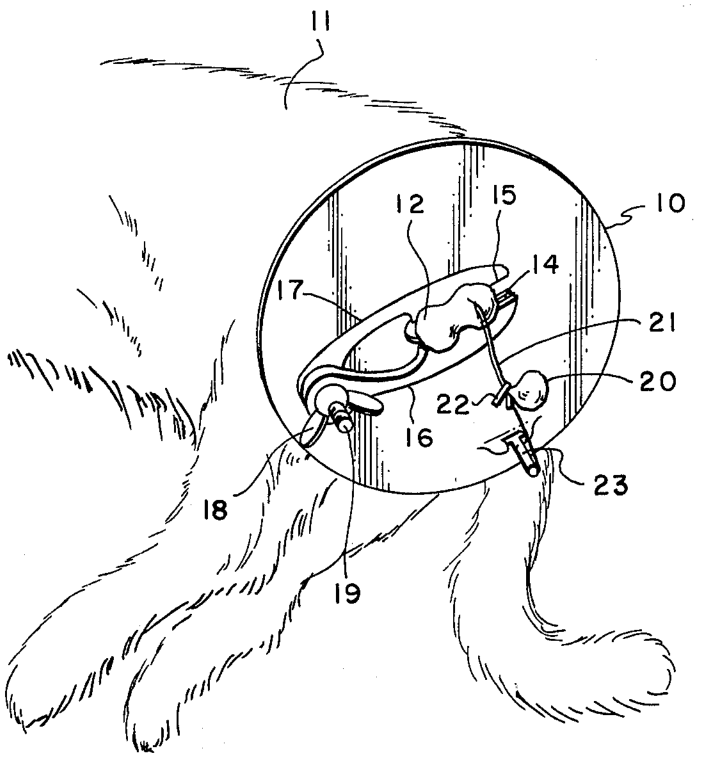
FIG. 1 is a perspective view of the apparatus of this invention showing its function and the operation of its components in a castration operation involving a feline animal.
Figure 2:
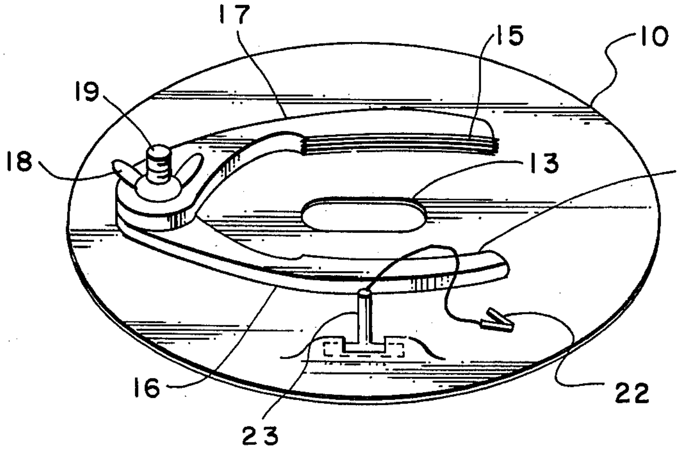
FIG. 2 is a perspective view of the apparatus of FIG. 1 illustrating the various components of the apparatus.

Some of the preferred embodiments of this invention can best be illustrated by referring to the drawings. As shown in FIG. 1, shield means 10 is in place over the genital area of an animal such as a male feline 11. With the shield apparatus in place as illustrated, scrotum 12 of the male feline 11 passes through aperture 13 (as more clearly illustrated in FIG. 2) such that scrotum 12 is adjacent the upper surface of shield 10. It will, of course, be appreciated that the view of shield 10 in FIGS. 1 and 2 is the upper surface of the shield means with the lower surface lying immediately below and not illustrated in FIGS. 1 and 2. Scrotum 12 is held in place by a suitable scrotum retaining means, which, in the illustrated embodiment in FIGS. 1 and 2, includes right jaw 14 and left jaw 15. Right jaw 14 is an integral part of one end of right arm 16 and left jaw 15 is an integral part of the terminal portion of left arm 17. The other ends of right arm 16 and left arm 17 are pivotally supported by and affixed to shield means 10 by means of pivot screw 19 which passes through suitable apertures in the ends of left and right arms 16 and 17. Pivot screw 19 is operably affixed to shield means 10 with wing nut 18 matingly engaging the threads of pivot screw 19. Thus, by loosening and tightening wing nut 18 on pivot screw 19, left and right arm 16 and 17 can be moved toward and away from each other across the upper surface of shield means 10 to thereby move right and left jaws 14 and 15 either apart or together in facingly opposing relationship.

In the operation of the apparatus of this invention, shield 10 is placed into position over the genital area of the animal with aperture 13 being immediately above scrotum 12. Then, by pressing shield 10 down over scrotum 12, the lower surface of shield 10 rests on and is supported by the body of the animal and scrotum 12 extends through aperture 13. With scrotum 12 extending through aperture 13, wing nut 18 can be loosened and right and left jaws 14 and 15 can be brought together to firmly engage and restrain scrotum 12 such that scrotum 12 is held firmly in place by jaws 14 and 15. With the scrotum held firmly in place, wing nut 18 can be tightened, thus restraining the scrotum adjacent the upper surface of the shield means.

As illustrated in FIG. 2, jaws 14 and 15 are shown in an opened relationship as would be utilized to apply the apparatus to the animal to be castrated. Of course, as soon as the scrotum 12 is extended through aperture 13, jaws 14 and 15 are brought into contact to engage and firmly secure and restrain the scrotum in position by the pivotal movement of right and left arms 16 and 17.

It will be appreciated that any suitable adjustment means can be utilized to adjust the position of arms 16 and 17 and to lock them into the desired relationship, either to open the arms or to close the arms to secure the scrotum in the desired position.

As soon as the apparatus is in place, as illustrated in FIG. 1, an incision can be made in scrotum 12 and testicle 20 can be withdrawn through the incision in the scrotum. In many animals, such as feline animals, as testicle 20 is withdrawn from the scrotum, spermatic cord 21 will also be withdrawn to a certain extent while it is still attached to testicle 20.

The apparatus of this invention also includes a suitable spermatic cord restraining means that is adapted to engage and restrain spermatic cord 21 when testicle 20 is withdrawn from scrotum 12. The spermatic cord restraining means can be any suitable means that will hold the spermatic cord in a position such that the spermatic cord can be sutured, or clamped if desired, and thereafter, severed to free the testicle for complete removal from the animal. In the illustrated embodiment, the spermatic cord restraining means includes a suitable cord clip 22 that is operably connected to cord arm 23. Cord clip 22, in the illustrated embodiment, is a small, V-notch clip that allows sperm cord 21 to be inserted into the open end of the V and, as it is pressed downward into the V, the walls of the V-notch will engage and restrain sperm cord 21. Of course, other suitable clips or clamps can be substituted for the illustrated cord clip 22. Cord clip 22 is affixed to one end of cord arm 23 with the other end of cord arm 23 being pivotally affixed to and supported by shield means 10. As illustrated, cord clip 22 is affixed to the upper end of cord arm 23 by means of a flexible member, such as a wire or plastic filament. As more clearly illustrated in FIG. 3, cord arm 23 is in the form of a T-shaped member with the lower portion of the T being journaled into suitable apertures in shield means 10. Thus, cord arm 23 is free to pivot about the base in such a manner that the upper end of cord arm 23 can move toward and away from aperture 13. In a preferred embodiment of the invention, cord arm 23 is operably affixed to a suitable spring 23A which is biased to urge the upper portion of cord arm 23 away from aperture 13. In the operation of such a preferred apparatus, cord arm 23 is pivoted toward aperture 13 with a force to overcome the biased spring 23A and cord clip 22 is brought into engagement with spermatic cord 21. Then, the action of the biased spring 23A will urge the upper portion of cord arm 23 away from aperture 13 to thereby hold spermatic cord 21 under tension, as illustrated in FIG. 1. With the spermatic cord under tension and elevated above the upper surface of shield means 10, a very simple procedure may be carried out wherein the veterinarian or other person performing the surgery can tie or clamp spermatic cord 21 into a closed condition without the need of an additional assistant to hold testicle 20 or spermatic cord 21 in place. Thus, the operation can be carried out without the need for an additional person to assist the veterinarian. Once the cord has been tied shut or clipped, if desired, the cord can then be severed and the testicle removed and then the remaining portion of the cord, affixed to the animal, can be reinserted into the scrotum. Once the procedure is completed, the scrotum can be sutured shut or appropriate medication can be applied to the area of the incision and the jaws 14 and 15 can be opened after which the entire apparatus is removed from the animal. All of these procedures can be carried out on an anesthetized animal by a single person, thus eliminating the need for two or more persons to assist in the operation.

An additional advantage of the invention, of course, is in the fact that the entire apparatus can be sterilized and the shield 10 serves as a very good surgical shield to isolate the scrotum from surrounding hair, fur, dirt, and other foreign bodies.

Figure 3:
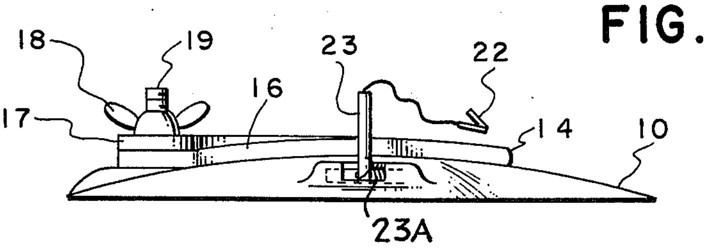
FIG. 3 is a side elevational view of the apparatus of FIGS. 1 and 2.

FIG. 3 is a side view of the apparatus of FIGS. 1 and 2, showing the upper surface of shield 10 as having a slightly convex shape. It has been found that the convex upper surface with a parallel concave lower surface of shield 10 is preferred for fitting the apparatus over the area of operation of the animal to be castrated. As shown in FIG. 3, left arm 17 is shaped to rest over the top of right arm 16 with the arms being of such a configuration that jaws 14 and 15 are positioned very close to the upper surface of shield 10 whereby the jaws can engage and restrain the scrotum of the animal to be castrated.

Shield 10 is preferably fabricated from a relatively rigid and relatively thin material such as thin-gauge metal, molded thermoplastics, and the like. As previously mentioned, it is preferably shaped such that the lower surface of the shield has a slightly concave configuration. The other components of the apparatus, such as the jaws and arms which engage the scrotum, as well as cord arm 23, can be made of any suitable, relatively rigid material, such as metal, heavy thermoplastics and the like. In some instances, it may be desirable to slightly roughen the inner faces of jaws 14 and 15 or provide them with suitable ribs to facilitate in the gripping or restraining of the scrotum to hold it securely in place above and immediately adjacent to the upper surface of shield 10.

Figure 4:
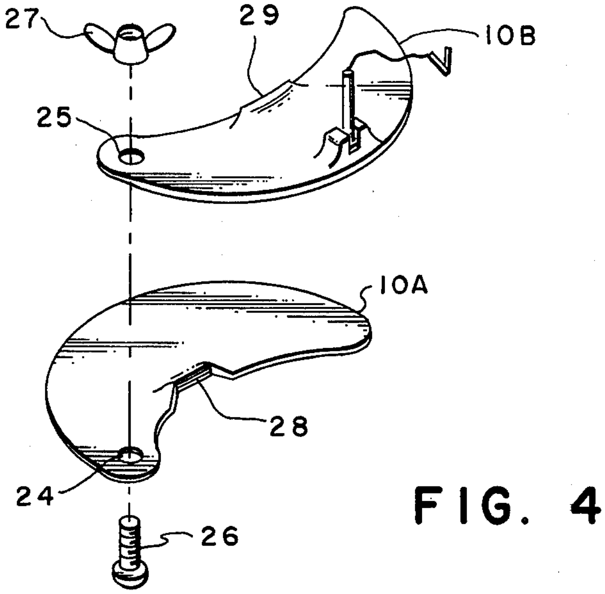
FIG. 4 is an exploded view of another embodiment of the invention wherein the shield means is made up of two movable sections.
Figure 5:
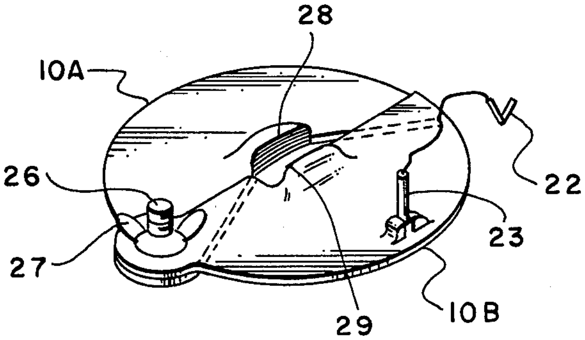
FIG. 5 is a perspective view of the components of FIG. 4 illustrating the assembled apparatus.

Another preferred embodiment of the invention is illustrated in FIGS. 4 and 5 wherein the shield means of the apparatus includes two shield sections 10*a* and 10*b*. Shields 10*a* and 10*b* are equipped with shield pivot apertures 24 and 25 through which shield adjusting screw 26 can be inserted. With the insertion of shield adjusting screw 26, shield adjusting nut 27 can be matingly engaged with the threads of the screw and, by loosening and tightening shield adjusting nut 27, the two sections 10*a* and 10*b* of the shield means are pivotally secured together about a pivot point, whereby the sections can pivot toward and away from each other in a common plane. Disposed along the facing edges of shield sections 10*a* and 10*b* are enlarged shoulders 28 and 29. Shoulders 28 and 29 are slightly recessed from the inner edges of shield sections 10*a* and 10*b*, whereby shoulders 28 and 29 define a suitable aperture between the facingly opposed edges of the shoulders as shield sections 10*a* and 10*b* are brought together, as illustrated in FIG. 5. With the slightly recessed shoulders 28 and 29, from the edges of the shield sections 10*a* and 10*b*, the aperture between such shoulders, when the shield sections 10*a* and 10*b* are brought together, define the aperture to receive and retain the scrotum of the animal to be castrated.

In the operation of the apparatus of FIGS. 4 and 5, the animal to be operated on is placed in a prone position and shield adjusting nut 27 is loosened to allow the apparatus to be fitted over the scrotum area of the animal and, once the scrotum is properly positioned, to contact either of shoulders 28 and 29, the shield sections 10*a* and 10*b* can be pivoted together in a common plane whereby the other shoulder will come into contact with the scrotum to engage and restrain the scrotum in a secure manner with the scrotum adjacent the upper surface of the shield means. By applying the proper amount of pressure to urge the shield means 10*a* and 10*b* together, the scrotum can be held securely in place and thereafter shield adjusting nut 27 can be tightened to hold the scrotum in place. The remaining operation of this apparatus is essentially the same as the apparatus described above in FIGS. 1 through 3.

While cord arm 23 has been illustrated as an arm means that is pivotally supported by shield means 10, the arm can be a simple arm that extends outwardly from the shield surface and rigidly attached to the shield. Thus, by bending the top of such an arm toward the aperture in the shield, the cord clip can engage the spermatic cord and the resilience of the bent arm will cause the bent arm to return to its original position, thus placing the spermatic cord under some degree of tension. Such an arm means that is an integral part of the shield means thus allows the entire shield and arm means to be molded from a material such as a thermoplastic as one unit by injection molding and the like.

It will be appreciated that the apparatus of this invention can be utilized for surgical operations involving several different types of animals. However, the apparatus has found particular utility in the castration procedures involving feline animals. It will also, of course, be appreciated that the appropriate sizes of the apparatus of this invention will vary according to the size of the animal to be operated on. Therefore, in normal veterinary practice, it will be expected that a veterinarian will have several different sizes of apparatus to accommodate animals of different size.

Various changes and modifications may be made in the foregoing disclosure without departing from the spirit and scope of this invention.

I claim:

1. An apparatus for use in the castration of an animal comprising:

a shield means having an upper surface and a lower surface with an aperture extending through said shield means, said aperture being adapted to receive the scrotum of said animal;

a scrotum retaining means adapted to engage and restrain said scrotum adjacent the upper surface of said shield means as said scrotum is pulled through said aperture; and a spermatic cord restraining means adapted to engage and restrain a spermatic cord of said animal in a predetermined position when a testicle is withdrawn from the scrotum, said spermatic cord restraining means including means to elevate and restrain said spermatic cord above the upper surface of said shield means and comprising a clip means to engage said spermatic cord, said clip means being operably affixed to the upper end of an arm means with the lower end of said arm means being affixed to and supported by said shield means.

2. The apparatus of claim 1 wherein said spermatic cord restraining means includes means adapted to restrain said spermatic cord under tension.

3. The apparatus of claim 1 wherein said lower end of said arm means is pivotally affixed to said shield means.

4. The apparatus of claim 1 wherein said scrotum retaining means comprises a pair of jaws, each jaw affixed to one end of each of a pair of arm means with the other end of each of said arm means being supported by and pivotally affixed to said shield means whereby said jaws can be brought into a facingly opposed position adjacent said aperture and above said upper surface of said shield.

5. The apparatus of claim 4 wherein adjustment means are operably affixed to said arms to adjust the position of said jaws in a predetermined position adjacent said aperture and to lock said jaws in said predetermined position.

6. The apparatus of claim 1 wherein said shield means is formed of two sections of relatively thin and substantially rigid material with said sections being pivotally secured together at a pivot point whereby said sections pivot toward and away from each other in a common plane with said aperture and said scrotum retaining means being formed by shoulders along the facingly opposed edges of said sections as said sections are pivoted together.

7. The apparatus of claim 1 further including spring means biased to urge the upper end of said arm means away from said aperture means.

* * * * *